:::

United States Patent [19]

Hino et al.

[11] Patent Number: 5,321,053

[45] Date of Patent: Jun. 14, 1994

[54] DENTAL COMPOSITIONS

[75] Inventors: Kenichi Hino; Junichi Yamauchi; Koji Nishida, all of Kurashiki, Japan

[73] Assignee: Kuraray Co., Ltd., Kurashiki, Japan

[21] Appl. No.: 475,903

[22] Filed: Feb. 6, 1990

Related U.S. Application Data

[63] Continuation of Ser. No. 63,804, Jun. 22, 1987, abandoned, which is a continuation of Ser. No. 708,943, Mar. 6, 1985, abandoned.

[30] Foreign Application Priority Data

Mar. 16, 1984 [JP] Japan .................................. 59-51883

[51] Int. Cl.⁵ ............................ C08F 2/50; C08F 4/40; C08F 30/02
[52] U.S. Cl. ......................................... 522/26; 522/14; 522/17; 522/16; 522/27; 522/83; 522/103; 522/168; 522/171; 523/116
[58] Field of Search ............................ 522/14, 16, 26

[56] References Cited

U.S. PATENT DOCUMENTS 4,499,251  2/1985  Omura et al. .................. 526/278
4,602,076  7/1986  Ratcliffe et al. ................ 522/13

FOREIGN PATENT DOCUMENTS 2337890  8/1977  France .

*Primary Examiner*—Marion E. McCamish
*Assistant Examiner*—Arthur H. Koeckert
*Attorney, Agent, or Firm*—Oblon, Spivak, McClelland, Maier & Neustadt

[57] ABSTRACT

A dental composition comprising a vinyl monomer containing at least one acidic group in the molecule thereof and an initiator capable of photopolymerizing said monomer by visible light, characterized in that said initiator consisting essentially of:

(a) a photosensitizer selected from an α-diketone, a quinone and a derivative thereof, and,
(b) an accelerator selected from a compound containing at least one mercapto group in the molecule thereof is provided by the present invention.

11 Claims, No Drawings

DENTAL COMPOSITIONS

This is a continuation of application Ser. No. 07/063,804, filed on Jun. 22, 1987, now abandoned, which is a continuation of Ser. No. 06/708,943, filed Mar. 6, 1985, now abandoned.

BACKGROUND OF THE INVENTION

1. Field of the Invention

The present invention relates to the polymerization and hardening of dental compositions which are adhesive towards tooth and dental restorative materials such as metals, ceramics, polymers, etc. and comprising monomers containing acidic groups in the molecule thereof by irradiating the dental compositions with visible light That is, the present invention relates to dental compositions comprising monomers containing acidic groups in the molecule thereof and polymerization initiators capable of polymerizing and hardening the monomers by irradiation of visible light.

2. Discussion of the Background

In dental treatment in recent years, an important technique has been the technique for adhesion to the tooth or metals. It is vinyl monomers containing acidic groups in the molecule thereof that plays the greatest role for enhancing the adhesive property In the case of using these monomers, the adhesion to the tooth or metals sufficiently reaches a level significant for dental treatment. Examples of such monomers include methacrylic acid esters containing in the molecule thereof aciding groups such as phosphoric or phosphonic acid diester groups, phosphoric or phosphonic acid mono ester groups, pyrrophosphoric acid groups, phosphinic acid groups, carboxyl groups, acid anhydride groups, acid halide groups, etc.

In recent dental techniques, attention has been focused upon a method for photohardening technique, in place of a conventional method using redox type polymerization initiators, as a method for hardening dental compositions. For this reason, it has been attempted to incorporate photopolymerization initiators into polymerizable monomer-containing compositions, in order to apply the photohardening method. As known photohardening techniques in the prior art, a method using α-diketones, etc. as sensitizers and amines as accelerators (U.S. Pat. No. 4,071,424), a method using benzoin alkyl ethers or benzyls as sensitizers and organic peroxides as accelerators (Japanese Patent Application OPI 102/80), a method using α-diketones as sensitizers and organic peroxides as accelerators (U.S. Pat. No. 4,459,193), etc. are known.

However, in the case of applying the catalyst systems using organic peroxides or tertiary amines as accelerators to photohardening of the above-mentioned polymerizable compositions containing the acidic group-containing monomers, irradiation to light requires a longer period of time than in the case of photopolymerizing conventional polymerizable compositions containing no acidic group-containing monomers but containing (meth)acrylic acid esters, which is not practical.

SUMMARY OF THE INVENTION

An object of the present invention is to provide compositions comprising vinyl monomers containing acidic groups in the molecule thereof having incorporated thereof highly efficient photopolymerization initiators capable of polymerizing and hardening the monomers by visible light, thereby causing the hardening of the dental compositions having adhesive property to the tooth and metals by photohardening.

Another object of the present invention is to provide a method for the restoration of the tooth cavity using dental compositions, as adhesive primers, comprising vinyl monomers containing acidic groups in the molecule thereof and initiators capable of photopolymerizing the monomers by visible light.

Such objects of the present invention are achieved by dental compositions comprising vinyl monomers containing at least one acidic group in the molecule thereof and initiators capable of photopolymerizing the monomers by visible light, characterized in that the initiators comprise (a) photosensitizers selected from α-diketones, quinones and derivatives thereof and (b) accelerators selected from compounds containing at least one mercapto group in the molecule thereof.

DETAILED DESCRIPTION OF THE INVENTION

The dental compositions of the present invention comprise vinyl monomers containing at least one acidic group in the molecule thereof, as described above.

The term "acidic group" as used herein refers to, in addition to narrowly defined acidic groups such as a —COOH group,

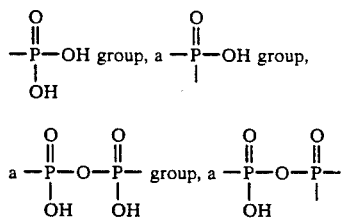

group, etc., an acid anhydride group such as a

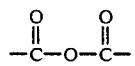

group, etc., an acid halide group such as a

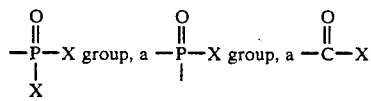

group (wherein X represents F, Cl, Br or I) and the like.

Specific examples of the monomers include the following compounds.

(1) A monomer having a

group:

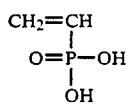

-continued
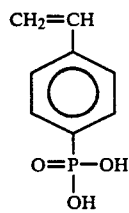
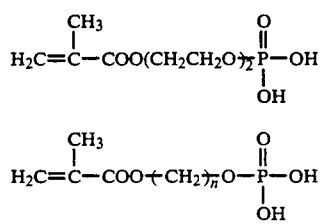
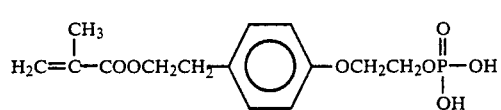
(wherein n is an integer of 2 to 40)
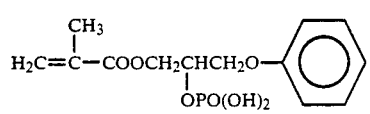
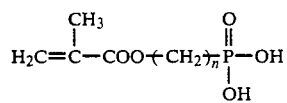
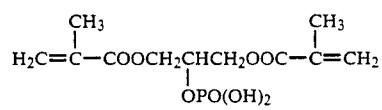
(wherein n is an integer of 2 to 40)
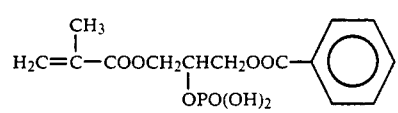
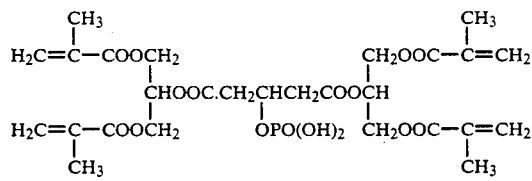
(2) A monomer having a
group:
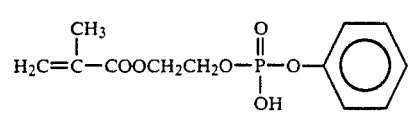
-continued
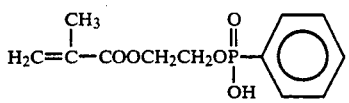
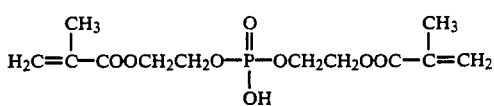
(3) (A monomer having a
group:
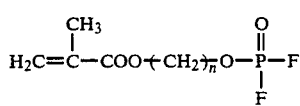
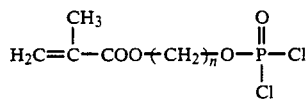
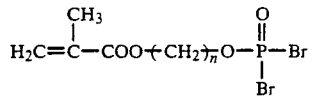
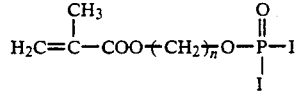
(wherein n is an integer of 2 to 20)
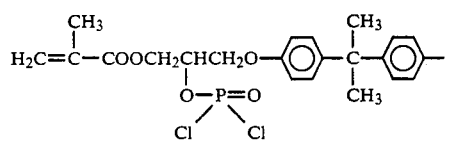
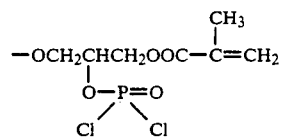
(4) A monomer having a
group:
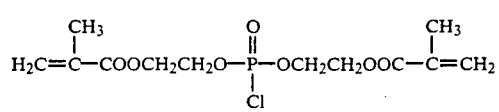

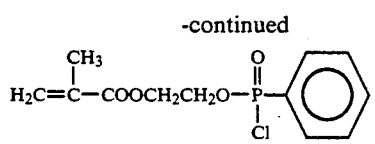
(5) A monomer having a
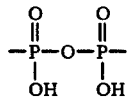
group:
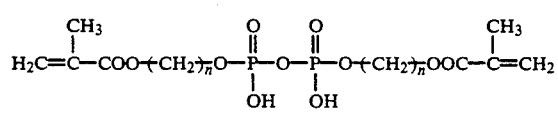
(wherein n is an integer of 2 to 20)
(6) A monomer having
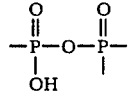
group:
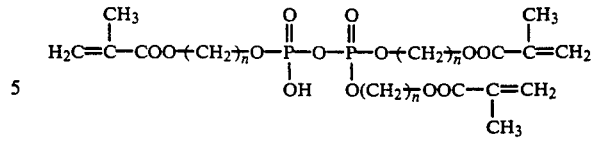
(wherein n is an integer of 2 to 20)
(7) A monomer having a —COOH group:
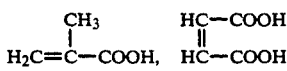
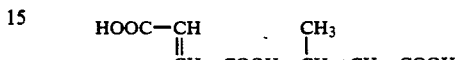
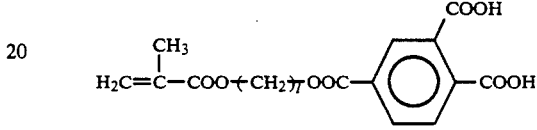
(wherein l is an integer of 2 to 12)
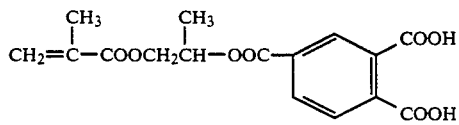
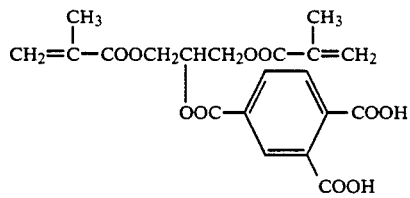
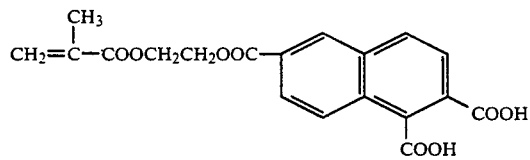
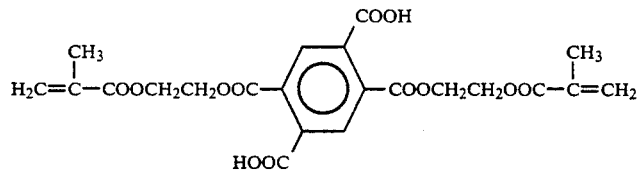
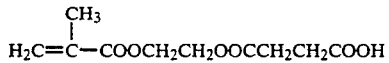
(8) A monomer having a
group:
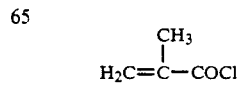

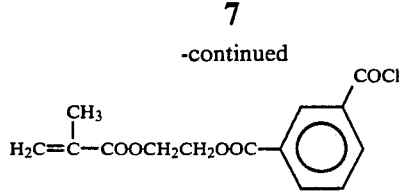

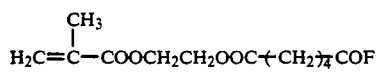

(9) A monomer having a $$-\overset{O}{\underset{\|}{C}}-O-\overset{O}{\underset{\|}{C}}-$$

group:

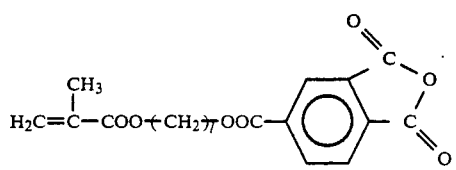

(wherein l is an integer of 2 to 12)

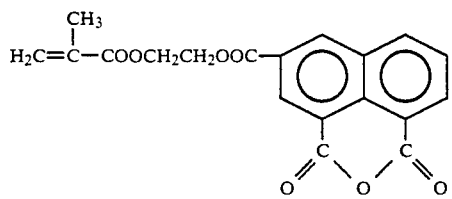

(ii) Bifunctional Esters
Esters shown by general formula:

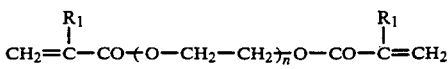

wherein n is an integer of 1 to 14 and $R_1$ is hydrogen or a methyl group; such as di(meth)acrylates of ethylene glycol, diethylene glycol, triethylene glycol (hereafter referred to as 3G), tetraethylene glycol, dodecaethylene glycol, tetradecaethylene glycol, etc., glycerine di(meth)acrylate, 2,2'-bis[p-(γ-methacryloxy-β-hydroxypropoxy)phenyl]propane (hereafter referred to as Bis-GMA), bisphenol A dimethacrylate, neopentylglycol di(meth)acrylate (hereafter referred to as NPG), 2,2'-di(4-methacryloxypolyethoxyphenyl)propane (containing 2 to 10 ethoxy groups in one molecule), 1,2-bis(3-methacryloxy-2-hydroxypropoxy)butane, etc.

(iii) Tri- or more-functinal Esters
Trimethylolpropane tri(meth)acrylate, pentaerythritol tetra(meth)acrylate, etc.

(iv) Urethane (Meth)acrylate Type
The reaction products of 2 moles of (meth)acrylate monomers having a hydroxyl group and 1 mole of diisocyanates, reaction products of urethane prepolymers having NCO at the terminals and (meth)acrylate monomers having a hydroxyl group, etc. Examples of such reaction products include those having the following structure:

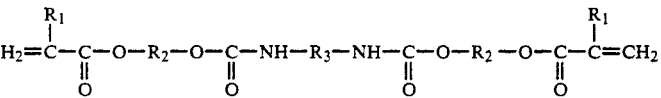

In the present invention, the monomers in the compositions may be composed of only monomers having the aforesaid acidic groups but generally, the monomers containing the acidic groups are used by formulating them in copolymerizable monomers later described. The monomers containing the acidic groups are formulated generally by more than 0.5 wt % in the total monomers in view of adhesive property. In the present invention, as vinyl monomers copolymerizable with the vinyl monomers containing the acidic groups, there are esters of α-cyanoacrylic acid, (meth)acrylic acid, urethane (meth)acrylic acid, crotonic acid, cinnamic acid, sorbic acid, maleic acid, itaconic acid, etc. with monovalent or bivalent alcohols; (meth)acrylamides such as N-isobutylacrylamide; vinyl esters of carboxylic acids such as vinyl acetate; vinyl ethers such as butyl vinyl ether; mono-N-vinyl compounds such as N-vinylpyrrolidone; styrene or derivative thereof; etc. In particular, esters of monofunctional or polyfunctional (meth)acrylic acids and urethane (meth)acrylic acid esters as described below are preferred.

(i) Monofunctional Esters
Methyl (meth)acrylate, n- or i-propyl (meth)acrylate, n- or i- or t-butyl (meth)acrylate, 2-hydroxyethyl methacrylate (hereafter referred to as HEMA), etc.

wherein $R_1$ is hydrogen or a methyl group, $R_2$ is an alkylene group and $R_3$ is an organic residue. Specific examples include the reaction product of 2,2,4-trimethylhexamethylenediisocyanate and oxypropyl methacrylate described in Japanese Patent Publication 36960/76, the reaction product of urethane prepolymer having isocyanates at the both terminals and 2-oxyethyl methacrylate described in Japanese Patent Publication 33687/80, etc. Further, tetrafunctional monomers as disclosed in U.S. Pat. No. 4,386,912 may also be employed.

The photosensitizer used in the present invention is at least one selected at from α-diketones, quinones and derivatives thereof, which have clear absorption at 380 to 500 nm in the UV and visible absorption spectrum. These sensitizers are represented by general formulae:

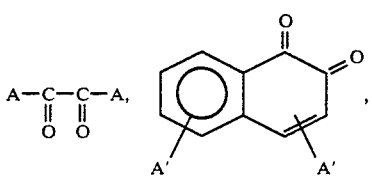

-continued

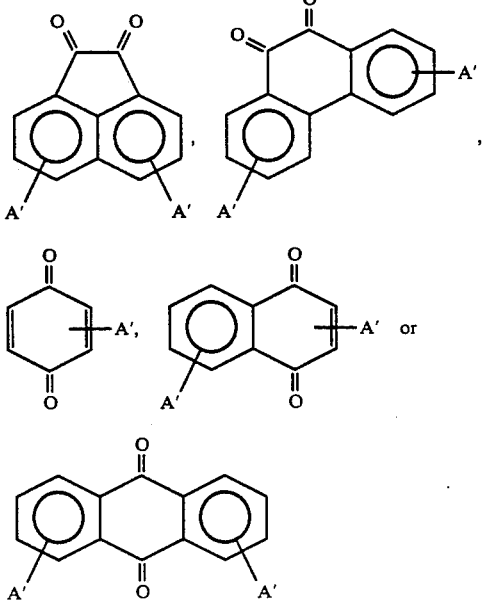

wherein A represents an aliphatic hydrocarbon residue having 1 to 20 carbon atoms wherein two A may be the same or different or two A may be combined with each other to form a cyclic structure; and A' represents 2 to 4 hydrogen atoms, an alkoxy group having 1 to 4 carbon atoms or an aliphatic hydrocarbon group having 1 to 20 carbon atoms wherein a plurality of ' may be the same or different. Examples of these sensitizers include acyclic α-diketones such as diacetyl, 2,3-pentanedione, 2,3- or 3,4-hexanedione, 2,3- or 3,4-heptanedione, 2,3-, 3,4- or 4,5-octanedione, etc ; alicyclic α-diketone compounds such as camphorquinone (the common name of 1,7,7-trimethylbicyclo[[2,2,1]heptane-2,3-dione), bicyclo[2,2,1]heptane-2,3-dione, etc.; further polycyclic quinones such as 9,10-phenanthraquinone, 9,10-anthraquinone, acenaphtheneinone, α- or β-naphthoquinone, etc.; derivatives of polycyclic quinones such as 2-methyl-1,4-naphthoquinone (vitamin K$_3$), 2-t-butyl-9,10-anthraquinone, 2-ethylanthraquinone, 1-chloroanthraquinone, 1,2-benzanthraquinone, 2-methylanthraquinone, 2-methyl-3-phytyl-1,4-naphthoquinone (vitamin K$_1$), 2-methyl-3-geranylgeranyl-1,4-naphthoquinone (vitamin K$_2$), 2,3-dimethoxy-5-methyl-1,4-benzoquinone (coenzyme Q$_0$), etc.

Of these quinones, camphorquinone , phenanthraquinone, acenaphthenequinone, β-naphthoquinone, anthraquinone, 2,3-pentanedione, 2,3- or 3,4-heptanedione, 2,3-, 3,4- or 4,5-octanedione, etc. are particularly preferred. These sensitizers are used in a range of 0.01 to 5 wt % based on the polymerizable monomers.

Next, the accelerator used in the present invention is a compound containing at least one mercapto group in the molecule thereof and includes the following compounds.

(a) Compounds represented by general formula:

B—SH wherein B represents an aliphatic hydrocarbon group having 1 to 20 carbon atoms or an aromatic hydrocarbon group having 6 to 20 carbon atoms; these hydrocarbon groups may have an alkyl group, an aryl group, a hydroxyl group, an alkoxy group, a carboxyl group, an alkoxycarbonyl group, an acyl group, a dialkylamino group, an amino group, a mercapto group, a halogeno group, a carbamoyl group, a nitro group, etc. wherein the alkyl, aryl, alkoxy, alkoxycarbonyl, acyl and dialkyl amino groups have 1 to 20 carbon atoms.

(b) Compounds represented by general formula:

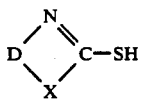

wherein D forms a 5- or 6-membered ring together with

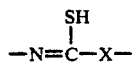

moiety and D is bound through a single bond or a double bond, or composed of 2 or 3 carbon atoms forming a part of one aromatic ring, or composed of one nitrogen atom bound to one carbon atom; and X represents —O—, —S—,

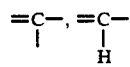

or NR (wherein R is H or a lower alkyl group having 1 to 4 carbon atoms).

(c) Compounds represented by general formula:

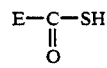

wherein E represents a phenyl group which may optionally contain a substituent having 1 to 20 carbon atoms or an alkyl group having 1 to 20 carbon atoms.

Specific examples of the photosensitizers include the following compounds.

Compounds shown in (a) above: alkyl mercaptans such as 1-octadecanethiol, 1-dodecanethiol, 1-eicosanethiol, etc.; cycloalkyl mercaptans such as cyclohexyl mercaptan, etc.; aryl mercaptans such as thiophenol, naphthalene-2-thiol, 2-naphthacenethiol, 4-cholanthrenethiol (1,2-dihydrobenz[h]-aceanthrylene-4-thiol), etc.; aryl alkyl mercaptans such as benzyl mercaptan, naphthacen-2-ylmethanethiol, 1,2-dihydrobenz[h]aceanthrylen-4-ylmethanethiol, etc.; alkyl aryl mercaptans such as thiocresol, butylbenzenethiol, p-eicosylthiophenol, p-phytylthiophenol, etc.; hydroxyl group-substituted mercaptans such as 2-mercaptoethanol, 3-mercapto-1,2-propanediol, etc.; alkoxy group-substituted mercaptans such as methoxybenzenethiol, 2-methoxyethanethiol, etc.; carboxyl group-substituted mercaptans such as 2-mercaptoacetic acid, 3-mercaptopropionic acid, thiosalicylic acid, etc.; alkoxycarbonyl group-substituted mercaptans such as ethyl 3-mercaptopropionate, etc.; acyl group-substituted mercaptans such as 4-mercaptoacetophenone, etc.; dialkylamino group-substituted mercaptans such as N,N-dimethylaminoethanethiol hydrochloride, N,N-diisopropylaminoethanethiol hydrochloride, etc.; amino group-substituted mercaptans such as 4-aminothiophenol, etc.; thiol group-containing mercaptans such as 1,4-butanedithiol, 1,9-nonanedithiol, etc.; halogen-substituted mercaptans such as chlorothiophenol, bromothiophenol, fluorothiophenol, etc.; carbamoyl group-substituted mercaptans such as 4-acetamidothiophenol, etc.; nitro group-substituted mercaptans such as 4-nitrothiophenol, etc.

Compounds represented by (b) above: 2-mercaptothiazoline, 2-mercaptopyridine, 2-mercaptoquinoline, 2-mercaptoimidazole, 2-mercapto-1-methylimidazole, 1-H-1,2,4-triazole-3-thiol, 2-mercaptobenzoxazole, 2-mercaptobenzothiazole, 2-mercaptobenzimidazole, 2-mercapto-1-ethylbenzimidazole, 2-mercapto-1-butylbenzimidazole, etc.

Compounds represented by (c) above: thiobenzoic acid, thiopropionic acid, heneicosanethioic S-acid, p-eicosylbenzenecarbothioic S-acid, etc.

In addition, furfuryl mercaptan and methylfurfurylmeracaptan may also be used.

These accelerators are used in a range of 0.1 to 10 wt % based on the polymerizable monomers, after the optimum concentration is determined depending upon polymerization system. In the present invention, the polymerization initiators may be composed of the above-mentioned two components (photosensitizers and accelerators).

The compositions of the present invention may be contain, in addition to the above-mentioned polymerizable monomers and photopolymerizable initiators, a variety of fillers depending upon purposes for which the composition is to be used. The fillers may be organic or inorganic; the organic fillers may be materials obtained by coating the inorganic fillers later described with polymers, in addition to methyl poly(meth)acrylates, ethyl poly(meth)acrylates, etc. The inorganic fillers may be powdery, fibrous or thin pieces composed of silicon dioxide, alumina, various glasses, ceramics, clay minerals such as diatomaceous earth, kaolin, montmorillonite, Japanese acid clay, etc.,synthetic zeolite, mica, calcium fluoride, calcium phosphate, barium sulfate, zirconium dioxide, titanium dioxide, etc. It is preferred that the largest particle size be under 500 m$\mu$. Further in the case of using the inorganic fillers, it is desired that they be used after surface treatment. As agent for the surface treatment, silane compounds such as $\gamma$-methacryloxypropyltrimethoxysilane, vinyltrichlorosilane, vinyltriethoxysilane, vinyltrimethoxysilane, vinyltriacetoxysilane, vinyltri(methoxyethoxy)silane, etc. are used; silanification may be carried out in a conventional manner. It is preferred to use these fillers in an amount of 1 to 7-fold weights based on the monomers.

Further the compositions of the present invention may be added, if necessary and desired, with polymerization inhibitors, coloring agents, UV absorbers, etc. The above-mentioned compositions may be generally supplied to dentists by previously mixing them in a paste or a solution and packing in a shielded container by the supplier. If necessary and desired, however, the compositions may be supplied by packing them in two containers. Dentists may apply the compositions of the present invention to the tooth and then allow to polymerize and harden them by visilbe light irradiated by an irradiator in a conventional manner.

As described above, the compositions of the present invention comprising the acidic group-containing monomers can be hardened at a rapid hardening rate by incorporating the above-mentioned specific photopolymerizable initiators. In addition, the compositions are excellent in stability during storage and are free from coloring of the hardened matters. Thus, the compositions have extremely excellent properties as compared to conventional photopolymerizable initiators. The compositions of the present invention are used as dental restorative materials. The dental restorative materials include not only dental filling composite materials for filling and restoring the tooth cavity but also dental crown materials, artificial teeth, dental adhesive agents, dental cementing materials, filling materials for preventing caries, etc.

It is particularly preferred to use the compositions of the present invention as dental adhesives coated on the surface of the tooth cavity prior to filling dental filling materials. In this case, the compositions of the present invention is firstly coated onto the surface of the tooth cavity which has or has not been etched with phosphoric acid, etc. and then the cavity is filled up with conventional dental filling materials. Hardening of the compositions of the present invention is carried out, after coating the compositions of the present invention and/or filling with filling materials, by irradiating with visible light.

The dental filling materials used together with the adhesives comprising the compositions of the present invention are generally composed of 10 to 80 wt % (preferably 15 to 50 wt %) of polymerizable monomers and 90 to 20 wt % (preferably 85 to 50 wt %) of the fillers. As the polymerizable monomers, the above-mentioned polymerizable monomers copolymerizable with the monomers containing acidic groups are used. Of these, the above-mentioned (meth)acrylic acid esters are preferred.

Further, a variety of fillers (quartz powders, etc.) as described above are used as the fillers. As initiators for the dental filling materials, redox catalysts composed of organic peroxides and amines which are of type hardened at room temperature can be used. Alternatively, photoinitiators such as camphorquinone—amines, etc. disclosed in U.S. Pat. No. 4,071,424 can be used. In case that polymerizable monomers having acidic groups in the molecule thereof are incorporated in polymerizable monomers for the dental filling materials, it is properly required that the above-mentioned photoinitiators in accordance with the present invention be incorporated. As described above, the adhesive is of photohardenable type and therefore, it is desired that the initiators for the dental filling materials be of photohardenable type.

In case that the polymerizable monomers hardened by the photoinitiators for the dental filling materials contain no acidic group in the molecule thereof, conventionally known photoinitiators disclosed in U.S. Pat. No. 4,071,424 supra can be used; however, it is most preferred to use photoinitiators (which comprise photosensitizers selected from $\alpha$-diketones and derivatives thereof and accelerators selected from aldehydes free of amino group and derivatives thereof; it is preferred to additionally incorporate organic peroxides such as benzoyl peroxide, etc. therein.) disclosed in the prior application (Japanese Patent Application 6797/84) according to the present inventors. The photoinitiators disclosed in the prior application can also harden the polymerizable monomers having acidic groups in the molecule thereof; however, the photoinitiators used in the present invention are more effective as initiators capable of photohardening such monomers.

In the photoinitiators disclosed in the prior application, $\alpha$-diketones, quinones and derivatives thereof are the same as the photosensitizers used in the present invention and are selected from the compounds as described above. As the aldehydes and derivatives thereof, it is desired that they be chosen from compounds represented by general formula:

B-(CHO)$_n$ wherein B represents an acyclic or cyclic saturated or unsaturated aliphatic hydrocarbon group having 1 to 20 carbon atoms or a monocyclic or polycyclic aromatic hydrocarbon group having 1 to 20 carbon atoms, in which these hydrocarbon groups may optionally have a substituent having 1 to 20 carbon atoms; and n is an integer of 1 to 3), an alkylmono- or di-aldehyde having 1 to 20 carbon atoms, a polyalkyl ether mono- or di-aldehyde having 1 to 20 carbon atoms and compounds represented by general formula:

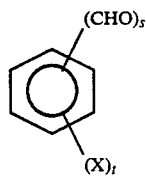

wherein s represents 1 or 2, X represents an alkyl, alkoxy or polyalkyl ether group having 1 to 20 carbon atoms and, t is 0 or an integer of 1 to 3.

As described above, in the case of using the compositions of the present invention as the dental adhesives, restoration of the tooth is effected in combination with the above-mentioned detanl filling materials. For this reason, it is preferred that dental doctors be provided with a set of the dental adhesives and the dental filling materials in combination for convenience.

Hereafter the present invention will be explained in more detail with reference to the examples but is not deemed to be limited to these examples.

EXAMPLE 1

A monomer mixture composed of 10 parts by weight of β-methacryloyloxyethylphenyl phosphoric acid:

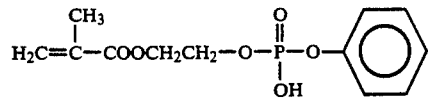

(hereafter referred to as Phenyl-P-monomer), 30 parts by weight of Bis-GMA, 30 parts by weight of HEMA and 30 parts by weight of NPG was prepared and camphorquinone was dissolved in the resulting monomer mixture in a concentration of 0.96 wt %. To the solution were added various mercaptans shown in Table 1, respectively, to prepare compositions and, each of the resulting composition was exposed to light, whereby a hardening time was measured.

Using as a light source Translux (15 V-150 W halogen lamp was used, in which light wavelengths longer than 500 nm were removed by a filter) made by Kulzer & Co. GmbH in Germany, a glass-made, cylindrical sample tube having a thickness of 0.8 mm in which the monomer composition was charged was located upward by 3.2 mm from the top and, light was irradiated from down. The measurement of hardening time was conducted by measuring change in temperature by inserting a thermocouple into the monomer mixture and, the point of time when increase of temperature due to polymerization heat ceased (the summit of the peak) was deemed to be a hardening time. In all of the following examples, the hardening time was determined using the aforesaid light source in the aforesaid method. The results are shown in Table 1.

TABLE 1

| Example | —SH group-containing Compound and Addition Amount Thereof (mg) | | Weight of Solution (mg) | Hardening Time (min) |
| --- | --- | --- | --- | --- |
| 1-1 | None (Control) | | 242.3 | >10 unhardened |
| 1-2 | CH$_3$-(CH$_2$)$_{10}$-CH$_2$SH | 3.2 | 220.5 | 2.67 |
| 1-3 | HO—CH$_2$CH$_2$—SH | 4.2 | 243.5 | 2.17 |
| 1-4 | HOOC—CH$_2$CH$_2$—SH | 3.3 | 227.4 | 2.25 |
| 1-5 | HS—CH$_2$—CH$_2$—SH | 3.1 | 233.8 | 2.00 |
| 1-6 | C$_6$H$_5$—CH$_2$—SH | 5.1 | 224.8 | 2.00 |
| 1-7 | C$_6$H$_5$—SH | 2.2 | 229.3 | 1.58 |
| 1-8 | naphthyl-SH | 4.2 | 237.2 | 1.78 |
| 1-9 | CH$_3$—C$_6$H$_4$—SH | 2.2 | 229.3 | 1.25 |

TABLE 1-continued

| Example | —SH group-containing Compound and Addition Amount Thereof (mg) | Weight of Solution (mg) | Hardening Time (min) |
|---|---|---|---|
| 1-10 | t-Bu—C₆H₄—SH, 1.9 | 234.2 | 0.50~1.00 |
| 1-11 | CH₃O—C₆H₄—SH, 3.6 | 230.2 | 2.05 |
| 1-12 | F—C₆H₄—SH, 4.1 | 224.1 | 1.67 |
| 1-13 | Cl—C₆H₄—SH, 5.0 | 222.8 | 1.83 |
| 1-14 | O₂N—C₆H₄—SH, 3.0 | 227.7 | 1.00 |
| 1-15 | o-HOOC—C₆H₄—SH, 2.9 | 219.6 | 1.08 |
| 1-16 | 2-mercaptobenzothiazole, 2.6 | 219.3 | 0.56 |
| 1-17 | 2-mercaptobenzimidazole, 2.4 | 223.4 | 0.63 |
| 1-18 | 2-mercaptobenzoxazole, 3.7 | 235.5 | 0.50 |
| 1-19 | 2-mercaptopyridine, 4.1 | 226.5 | 0.88 |
| 1-20 | C₆H₅—C(=O)—SH, 5.3 | 226.9 | 0.55 |
| 1-21 | CH₃CH₂—C(=O)—SH, 4.8 | 233.3 | 0.67 |

EXAMPLE 2

A composition composed of 9.9 parts by weight of Phenyl-P-monomer, 29.7 parts by weight of HEMA, 29.7 parts by weight of Bis-GMA, 29.7 parts by weight of NPG and 1.0 part by weight of 2-mercaptobenzimidazole was prepared and, various photosensitizers shown in Table 2 were added to the composition, respectively. In a manner similar to Example 1, visible light was exposed to each of the resulting compositions to determine a hardening time.

TABLE 2

| Example | Photoinitiator | Concentration of Photoinitiator (wt %) based on composition | Hardening Time (minute) |
|---|---|---|---|
| 2-1 | Camphorquinone | 0.97 | 0.63 |
| 2-2 | Acenaphthenequinone | 1.00 | 0.95 |
| 2-3 | 1,2-Benzanthraquinone | 0.97 | 0.88 |
| 2-4 | 2-Methylanthraquinone | 1.04 | 0.95 |
| 2-5 | Heptanedione | 1.96 | 1.50 |
| 2-6 | Benzil | 1.97 | 1.63 |
| 2-7 | Phenanthraquinone | 0.10 | 2.00 |

EXAMPLE 3

A solution was prepared by dissolving camphorquinone, in a concentration of 1.00 wt %, in a monomer mixture composed of 10 parts by weight of C-10 P monomer:

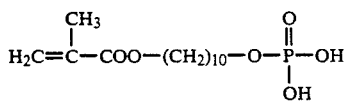

30 parts by weight of Bis-GMA, 30 parts by weight of HEMA and 30 parts by weight of NPG. To the solution were added various mercaptans shown in Table 2, respectively, to prepare compositions and, the resulting compositions were exposed to light to determine hardening times. The results are shown in Table 3.

TABLE 3

| Example | —SH Compound and Addition Amount Thereof (mg) | Weight of Solution (mg) | Hardening Time (min) |
|---|---|---|---|
| 3-1 | Control | 224.3 | 9.00 |
| 3-2 | C₆H₅—SH | 3.2 | 237.0 | 0.75 |
| 3-3 | t-Bu-C₆H₄—SH | 3.3 | 233.6 | 1.03 |
| 3-4 | 2-mercaptopyridine | 1.6 | 239.6 | 0.58 |
| 3-5 | 2-mercaptobenzimidazole | 3.1 | 226.5 | 0.25 |
| 3-6 | 2-mercaptobenzothiazole | 2.8 | 233.7 | 0.47 |
| 3-7 | 2-mercaptobenzoxazole | 3.4 | 226.3 | 0.40 |

EXAMPLE 4

Using monomer mixtures having compositions described in Table 4 and using sensitizers and accelerators shown in Table 4, the procedures of Example 1 were repeated. The results are shown in Table 4.

TABLE 4

| Example | Composition of Monomer (part by wt.) | | Kind of Sensitizer & Addition Amount (wt %) | Wt. of Composition (mg) | Kind of Accelerator and Addition Amount (mg) | | Hardening Time (min) |
|---|---|---|---|---|---|---|---|
| 4-1 | Cinnamic acid<br>TMM-3L**<br>Epoxy ester 3002* | 8.00<br>23.00<br>69.00 | Diacetyl m | 1.72 | 225.6 | 4-t-Butylthiophenol | 3.4 | 0.83 |
| 4-2 | Cinnamic acid<br>TMM-3L**<br>Epoxy ester 3002* | | Phenanthraquinone | 0.18 | 235.4 | 4-t-Butylthiophenol | 2.6 | 0.83 |
| 4-3 | Crotonic acid<br>Bis-GMA<br>Triethyleneglycol dimethacrylate | 9.09<br>69.09<br>21.82 | 2,3-Pentanedione | 1.31 | 221.7 | 4-t-Butylthiophenol | 4.3 | 0.67 |
| 4-4 | Crotonic acid<br>Bis-GMA<br>Triethyleneglycol dimethacrylate | | 2-Methyl-1,4-naphthoquinone (vitamin K₃) | 0.56 | 222.1 | 4-t-Butylthiophenol | 4.9 | 1.50 |
| 4-5 | Phenyl-P-monomer<br>TMM-3L<br>Epoxy ester 3002 | 9.47<br>22.63<br>67.90 | Acenaphthenequinone | 0.26 | 248.8 | 4-t-Butylthiophenol | 4.7 | 0.58 |
| 4-6 | Phenyl-P-monomer<br>TMM-3L<br>Epoxy ester 3002 | | 2,3-Dimethoxy-5-methyl-1,4-benzoquinone (CoQo) | 0.20 | 228.1 | 4-t-Butylthiophenol | 2.3 | 2.70 |
| 4-7 | Phenyl-P-monomer<br>TMM-3L<br>Epoxy ester 3002 | | 2-Methylanthraquinone | 1.84 | 230.4 | 4-t-Butylthiophenol | 3.1 | 0.75 |
| 4-8 | Phenyl-P-monomer<br>TMM-3L<br>Epoxy ester 3002 | | β-Naphthoquinone | 0.06 | 261.3 | 4-t-Butylthiophenol | 5.1 | 1.17 |
| 4-9 | Methacrylic chloride<br>Bis-GMA<br>Triethyleneglycol | 8.91<br>69.23<br>21.86 | 2,3-Heptanedione | 2.11 | 216.1 | 2-Mercaptobenzimidazole | 4.3 | 0.47 |

TABLE 4-continued

| Example | Composition of Monomer (part by wt.) | | Kind of Sensitizer & Addition Amount (wt %) | Wt. of Composition (mg) | Kind of Accelerator and Addition Amount (mg) | | Hardening Time (min) |
|---|---|---|---|---|---|---|---|
| 4-10 | dimethacrylate JPA-monomer*** Bis-GMA Triethyleneglycol dimethacrylate | 9.71 68.62 21.67 | 2,3-Heptanedione 1.33 | 229.7 | 2-Mercapto- benzimidazole | 5.0 | 0.33 |

*Epoxy ester 3002: structural formula $$\text{CH}_2=\text{C(CH}_3\text{)COOCH}_2\text{CH(OH)CH}_2\text{OCH}_2\text{CH(CH}_3\text{)CH}_2\text{O}-\text{C}_6\text{H}_4-\text{C(CH}_3)_2-\text{C}_6\text{H}_4-\text{OCH}_2\text{CH(CH}_3\text{)CH}_2\text{O}-\text{CH}_2-\text{CH(OH)CH}_2\text{OOC-C(CH}_3\text{)=CH}_2$$

**TMM-3L: Pentaerythritol trimethacrylate

***JPA monomer: structural formula:

$$\text{CH}_2=\text{C(CH}_3\text{)COOCH}_2\text{CH}_2-\text{O}-\overset{\text{O}}{\underset{\text{OH}}{\text{P}}}-\text{O}-\text{CH}_2\text{CH}_2\text{OOC-C(CH}_3\text{)=CH}_2$$

EXAMPLE 5

A composite resin was prepared according to the following composition.

| Composition: | |
|---|---|
| Phenyl-P-monomer | 0.1138 g |
| TMM-3L | 0.2720 g |
| Epoxy ester 3002 | 0.8161 g |
| Camphorquinone | 0.006 g |
| Mercaptobenzoxazole | 0.0122 g |
| Silane treated quartz powder | 3.9210 g |
| Colloidal silica | 0.050 g |

These various components were kneaded in a mortar to prepare a paste. After the paste was degassed in a vaccum in a desicator, the paste was filled up in a glass tube having an inner diameter of 3 mm in a length of 12 mm. From one side of the glass tube, light was irradiated for 10 seconds at a distance of 4 mm using the light source described in Example 1. Thereafter a needle having a diameter of 1 mm was inserted from the other side of the glass tube to which no light was exposed and, a load of 260 g was applied to the needle for 30 seconds to measure the degree of the needle penetrated, whereby the thickness of the hardened portion was measured. The composite resin of 7 mm was hardened.

EXAMPLE 6

A bonding agent and a composite resin were prepared according to the following compositions:

| Composition 1: Bonding Agent | |
|---|---|
| Bis-GMA | 30 parts by weight |
| NPG | 30 parts by weight |
| HEMA | 30 parts by weight |
| Phenyl-P-monomer | 10 parts by weight |
| Camphorquinone | 1.5 part by weight |
| Mercaptobenzothiazole | 1.5 part by weight |
| Composition 2: Composite Resin | |
| Bis-GMA | 17.33 parts by weight |
| 3G | 5.77 parts by weight |
| Camphorquinone | 0.34 part by weight |
| Mercaptobenzothiazole | 0.34 part by weight |
| Silane treated quartz powder | 73.96 parts by weight |
| Colloidal silica | 2.26 parts by weight |

The thus prepared bonding agent and the composite resin were combined together to determine adhesion force to ivory bars. Adhesion test to the ivory bars was performed by the following method. First, the edge surfaces of two ivory bars (10×10×50 mm) were abraded with emery paper. After rinsing with water, the bonding agent was thinly coated on to the abraded surfaces using a small brush. Then, a paste of the composite resin was put in a layer onto the surface coated with the bonding agent, using a CR-syringe, which was exposed to light for 2 minutes using the light source described in Example 1. Next, the photohardened resin portion was adhered to other ivory bar using a conventional dental composite resin (registered trademark: Clearfill FII). After soaking it in water at 37° C. overnight, it was subjected to a tensile test using Instron tensile tester. The adhered matter showed an adhesion force of 47.6 kg/cm$^2$.

COMPARISON EXAMPLE 1

A solution was prepared by dissolving camphorquinone (0.97 wt %) and N,N-dimethyl-p-toluidine (0.99 wt %) in a monomer mixture composed of 30 parts by weight of Bis-GMA, 30 parts by weight of NPG and 40 parts by weight of HEMA. Phenyl-P-monomer was added to the solution in an amount shown in Table 5 to obtain composition. The composition was exposed to light to measure a hardening time. For purpose of comparison, the results obtained by adding no Phenyl-P-monomer are also shown.

TABLE 5

| Comparison Example | Weight of Phenyl-P- monomer (mg) | Weight of Solution (mg) | Hardening Time (sec) |
|---|---|---|---|
| 1-1 | 0 | 227.4 | 68 |
| 1-2 | 27 | 220 | 200 |

COMPARISON EXAMPLE 2

A solution was obtained by dissolving camphorquinone (0.90 wt %) and benzoyl peroxide (0.79 wt %) in the same monomer mixture as in Comparison Example 1 and, methacrylic acid was added thereto in an amount described in Table 6. The resulting composition was exposed to light to measure a hardening time. For purpose of comparison, the results obtained by adding no methacrylic acid are also shown.

TABLE 6

| Comparison Example | Weight of Methacrylic Acid (mg) | Weight of Solution (mg) | Hardening Time (sec) |
|---|---|---|---|
| 2-1 | 0 | 224.1 | 51 |

TABLE 6-continued

| Comparison Example | Weight of Methacrylic Acid (mg) | Weight of Solution (mg) | Hardening Time (sec) |
|---|---|---|---|
| 2-2 | 10.1 | 218 | 210 |

COMPARISON EXAMPLE 3

A solution was prepared by dissolving 0.06 wt % of β-naphthoquinone in a monomer mixture composed of 9.47 parts by weight of Phenyl-P-monomer, 22.63 parts by weight of pentaerythritol trimethyacrylate and 67.90 parts by weight of epoxy ester 3002 and, amines shown in Table 7 were added thereto. The resulting compositions were exposed to light to measure hardening times. The results are shown in Table 7.

TABLE 7

| Comparison Example | Kind of Amine and Addition Amount Thereof (mg) | | Amount of Monomer Mixture (mg) | Hardening Time (min) |
|---|---|---|---|---|
| 3-1 | None (control) | | 231.0 | 4.00 |
| 3-2 | Triethanolamine | 7.5 | 273.3 | 4.00–5.00 |
| 3-3 | N,N-Dimethyl-aminoethyl methacrylate | 6.5 | 219.2 | 3.67–4.00 |
| 3-4 | Triethylamine | 15 | 248.0 | 4.00–4.33 |

EXAMPLE 7

A bonding agent and a composite resin were prepared according to the following compositions.

| Composition 3: Bonding Agent | |
|---|---|
| Bis-GMA | 50 parts by weight |
| C-10 P monomer | 5 parts by weight |
| NPG | 15 parts by weight |
| HEMA | 30 parts by weight |
| Camphorquinone | 1 part by weight |
| Mercaptobenzoxazole | 1 part by weight |
| Composition 4A: Composite Resin | |
| Bis-GMA | 10 parts by weight |
| 3G | 4 parts by weight |
| Camphorquinone | 0.1 part by weight |
| Benzoyl peroxide | 0.15 part by weight |
| p-Tolualdehyde | 0.3 part by weight |
| Silane treated quartz powder | 79 parts by weight |
| Colloidal silica | 4 parts by weight |
| Composition 4B: Composite Resin | |
| Bis-GMA | 10 parts by weight |
| 3G | 4 parts by weight |
| Camphorquinone | 0.1 part by weight |
| N,N-Dimethylamino-ethyl methacrylate | 0.3 part by weight |
| Silane treated quartz powder | 79 parts by weight |
| Colloidal silica | 4 parts by weight |

The thus obtained bonding agent and the composite resin A or B were combined together to determine adhesion force to ivory bars. The ivory bars were treated in a manner similar to Example 6. After the bonding agent was thinly coated onto the edge surfaces of the ivory bars, about 0.3 g of a paste of the composite resin was put on the coated surfaces and the paste was spread over the whole edge surfaces of the ivory bars using a glass piece to form a paste layer having a thickness of 1 mm. Thereafter, light was irradiated for 40 seconds using the light source described in Example 1. About 5 minutes after, the glass ivory bar was adhered to the hardened resin using commercially available dental composite resin (registered Clearfill FII). After soaking it in water at 37° C. overnight, adhesion force was measured using Instron tensile tester. Compositions A and B gave adhesion strengths of 130 kg/cm² and 90 kg/cm², respectively.

EXAMPLE 8

Using the bonding agent having Composition 3 prepared in Example 7 and a composite resin (paste type) having the following composition, adhesion force to ivory bars was determined.

| Composition 5: | |
|---|---|
| Bis-GMA | 10 parts by weight |
| 3G | 4 parts by weight |
| Benzoyl peroxide | 0.25 part by weight |
| Silane treated quartz powder | 79 parts by weight |
| Colloidal silica | 4 parts by weight |
| Composition 6: | |
| Bis-GMA | 10 parts by weight |
| 3G | 4 parts by weight |
| N,N-Diethanol-p-toluidine | 0.12 part by weight |
| Silane treated quartz powder | 79 parts by weight |
| Colloidal silica | 4 parts by weight |

Two ivory bars treated in a manner similar to Example 6 were prepared. At the edge surface of each of the bars, the bonding agent having Composition 3 was thinly coated and, light was irradiated for 20 seconds using Translux to harden the above-mentioned bonding agent. Then, a paste obtained by kneading composite resins of Compositions 5 and 6 was put on the hardened portion. Thereafter two ivory bars were brought into close contact and allowed to stand for 10 minutes at 25° C. After soaking it in water at 37° C. overnight, adhesion force was measured using Instron tensile tester. Adhesion strength of 80 kg/cm² was obtained

COMPARISON EXAMPLE 4

Allylthiourea which is used as a photoaccelator for a dental composition containing an acidic group-having monomer in Japanese Patent Application Laid Open 56-120610 was added to Composition 3 of Example 7, in place of mercaptobenzoxazole. The thus obtained bonding agent and the composite resin A of Example 7 were combined together to determine adhesion force to ivory bars. The adhesion force was measured in the same manner of Example 7. The composition gave adhesion strength of 70 Kg/cm².

While the invention has been described in detail and with reference to specific embodiments thereof, it will be apparent to one skilled in the art that various changes and modifications can be made therein without departing from the spirit and scope thereof.

What is claimed is:

1. A dental composition, comprising:
   (i) a vinyl monomer containing at least one acidic group selected from the group consisting of:

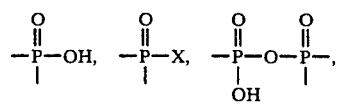

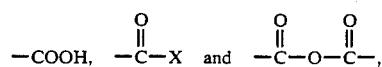

wherein X represents a halogen atom, and (ii) an initiator which photopolymerizes said monomer by visible light, wherein said initiator comprises:
(a) an α-diketone and
(b) an accelerator which is at least one member selected from the group consisting of 2-mercaptobenzoxazole, 2-mercaptobenzothiazole and 2-mercaptobenzimidazole.

2. The dental composition of claim 1, wherein said initiator comprises (a) camphorquinone, and (b) 2-mercaptobenzimidazole, 2-mercaptobenzothiazole, or 2-mercaptobenzoxazole.

3. The dental composition of claim 1, wherein said initiator comprises camphorquinone.

4. The dental composition of claim 1, wherein component (i) comprises said vinyl monomer and an ester of a monofunctional or polyfunctional (meth)acrylic acid.

5. The dental composition of claim 4, wherein said component (i) comprises triethylene glycol dimethylacrylate (3G), or 2,2-bis[4-(3-methacryloyloxypropoxy)-phenyl]propane (bis-GMA).

6. The dental composition of claim 5, wherein said initiator comprises (a) camphorquinone, and (b) 2-mercaptobenzimidazole, 2-mercaptobenzothiazole, or 2-mercaptobenzoxazole.

7. The dental composition of claim 1, wherein said acidic group is an acidic group selected from the group consisting of

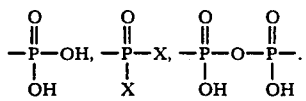

8. The dental composition of claim 1, wherein a vinyl monomer copolymerizable with said vinyl monomer containing at least one acidic group is incorporated in said composition.

9. The dental composition of claim 1, comprising a filler.

10. The composition of claim 1, wherein said vinyl monomer is $H_2C=C(CH_3)-COO-(CH_2)_{10}-OP(O)(OH)_2$.

11. A dental composition, comprising:
(i) a vinyl monomer containing at least one acidic group, said vinyl monomer being beta-methacryloyloxyethylphenyl phosphoric acid; and
(ii) an initiator capable of photopolymerizing said monomer by visible light, wherein said initiator consists essentially of: (a) camphorquinone and (b) 2-mercaptobenzoxazole.

* * * * *